United States Patent
Decoster et al.

(10) Patent No.: US 8,470,754 B2
(45) Date of Patent: Jun. 25, 2013

(54) DETERGENT COSMETIC COMPOSITIONS COMPRISING AT LEAST ONE AMINO SILICONE, AND USES THEREOF

(75) Inventors: Sandrine Decoster, Saint Gratien (FR); Stéphanie Neplaz, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/498,625

(22) Filed: Jul. 7, 2009

(65) Prior Publication Data

US 2010/0035782 A1 Feb. 11, 2010

Related U.S. Application Data

(60) Provisional application No. 61/129,640, filed on Jul. 9, 2008.

(30) Foreign Application Priority Data

Jul. 8, 2008 (FR) .................................... 08 54633

(51) Int. Cl.
*C11D 1/94* (2006.01)
*C11D 9/36* (2006.01)

(52) U.S. Cl.
USPC ........... 510/124; 510/119; 510/122; 510/123; 510/125; 510/127; 510/130; 510/426; 510/427; 510/466; 510/490

(58) Field of Classification Search
USPC ................. 510/119, 122, 123, 124, 125, 127, 510/130, 426, 427, 466, 490
See application file for complete search history.

(56) References Cited

U.S. PATENT DOCUMENTS

| | | | |
|---|---|---|---|
| 3,950,417 A | 4/1976 | Verdicchio et al. | |
| 6,033,652 A * | 3/2000 | Ansmann | 424/70.122 |
| 6,153,569 A | 11/2000 | Halloran | |
| 6,159,914 A | 12/2000 | DeCoster et al. | |
| 6,475,499 B2 | 11/2002 | Maubru et al. | |
| 6,726,902 B1 | 4/2004 | Muller et al. | |
| 6,808,701 B2 | 10/2004 | Duden et al. | |
| 6,824,764 B2 | 11/2004 | Devin-Baudoin et al. | |
| 6,824,765 B2 | 11/2004 | Gawtrey et al. | |
| 7,179,452 B2 | 2/2007 | Muller et al. | |
| 2001/0009909 A1 | 7/2001 | Maubru et al. | |
| 2002/0006389 A1 | 1/2002 | Restle et al. | |
| 2003/0108501 A1 | 6/2003 | Hofrichter et al. | |
| 2003/0129155 A1 * | 7/2003 | Devin-Baudoin et al. | 424/70.2 |
| 2003/0134760 A1 | 7/2003 | Harrison et al. | |
| 2003/0157049 A1 * | 8/2003 | Gawtrey et al. | 424/70.122 |
| 2004/0170593 A1 | 9/2004 | Muller et al. | |
| 2004/0258653 A1 * | 12/2004 | Sakai et al. | 424/70.31 |
| 2005/0019299 A1 * | 1/2005 | LiBrizzi et al. | 424/70.17 |
| 2005/0063934 A1 | 3/2005 | Baker et al. | |
| 2005/0232885 A1 | 10/2005 | Samain et al. | |
| 2006/0019858 A1 * | 1/2006 | Kruse et al. | 510/424 |
| 2006/0275245 A1 * | 12/2006 | Decoster et al. | 424/70.122 |
| 2007/0009461 A1 * | 1/2007 | Chandra et al. | 424/70.1 |
| 2007/0041930 A1 | 2/2007 | Meder et al. | |
| 2007/0077221 A1 * | 4/2007 | Seigneurin et al. | 424/70.16 |
| 2007/0258936 A1 * | 11/2007 | Decoster et al. | 424/70.12 |
| 2008/0171684 A1 * | 7/2008 | Boutique et al. | 510/299 |
| 2008/0276385 A1 * | 11/2008 | Cottard et al. | 8/408 |
| 2008/0311066 A1 * | 12/2008 | Samain et al. | 424/70.16 |
| 2009/0000638 A1 * | 1/2009 | Wood et al. | 132/205 |
| 2009/0074699 A1 * | 3/2009 | Biganska et al. | 424/70.16 |
| 2009/0130028 A1 * | 5/2009 | Rollat-Corvol et al. | 424/47 |

FOREIGN PATENT DOCUMENTS

| | | |
|---|---|---|
| EP | 0 453 238 | 10/1991 |
| EP | 0 697 206 | 2/1996 |
| EP | 0 870 491 | 10/1998 |
| EP | 0 974 335 | 1/2000 |
| EP | 1 136 066 | 9/2001 |
| EP | 1 312 345 | 5/2003 |
| EP | 1 312 346 | 5/2003 |
| EP | 1 321 131 | 6/2003 |
| EP | 1 543 820 | 6/2005 |
| EP | 1 726 294 | 11/2006 |
| EP | 1 726 295 | 11/2006 |
| EP | 1 849 453 | 10/2007 |
| FR | 2 785 181 | 5/2000 |
| FR | 2 804 020 | 7/2001 |
| FR | 2 864 767 | 7/2005 |
| WO | WO 95/26707 | 10/1995 |
| WO | WO 2006/065469 | 6/2006 |

OTHER PUBLICATIONS

Anonymous, "Cosmetic Raw Materials," Clariant Personal Care Brochure, (2006).

(Continued)

*Primary Examiner* — Charles Boyer
(74) *Attorney, Agent, or Firm* — O'Brien Jones, PLLC.

(57) ABSTRACT

The disclosure relates to novel detergent compositions comprising, in a cosmetically acceptable medium, (A) at least one sulfate or sulfonate anionic surfactant, (B) at least one surfactant chosen from amphoteric and zwitterionic surfactants and (C) at least one amino silicone with a weight-average molecular mass Mw greater than or equal to 75,000, the (sulfate or sulfonate anionic surfactant)/(amphoteric and/or zwitterionic surfactant) weight ratio ranging from 1:1 to 2:1, the total amount of surfactants representing from 4% to 35% by weight relative to the total weight of the final composition. The disclosure also relates to the use of the composition for protecting the coloration of artificially dyed hair.

23 Claims, No Drawings

OTHER PUBLICATIONS

Copending Application titled "Detergent Cosmetic Compositions Comprising an Amino Silicone, and Use Thereof," filed Jul. 7, 2009, Inventors: Sandrine Decoster et al.
English language Abstract of EP 1 321 131, dated Jun. 25, 2003.
English language Abstract of EP 1 726 294, dated Nov. 29, 2006.
English language Abstract of EP 1 726 295, dated Nov. 29, 2006.
French Search Report for FR 08/54633, dated Mar. 4, 2009.
French Search Report for FR 08/54634, dated Mar. 5, 2009.
Copending U.S. Appl. No. 11/790,936, filed Apr. 30, 2007.
English language Abstract of EP 0 697 206, dated Feb. 21, 1996.
French Search Report for FR 06/03848, dated Dec. 20, 2006.
Office Action mailed Dec. 22, 2010, in co-pending U.S. Appl. No. 12/498,582.
Office Action mailed Nov. 27, 2009, in co-pending U.S. Appl. No. 11/790,936.
Office Action mailed Sep. 9, 2010, in co-pending U.S. Appl. No. 11/790,936.
Office Action mailed Aug. 12, 2011, in co-pending U.S. Appl. No. 12/498,582.

* cited by examiner

DETERGENT COSMETIC COMPOSITIONS COMPRISING AT LEAST ONE AMINO SILICONE, AND USES THEREOF

This application claims benefit of U.S. Provisional Application No. 61/129,640, filed Jul. 9, 2008, the contents of which are incorporated herein by reference. This application also claims benefit of priority under 35 U.S.C. §119 to French Patent Application No. FR 0854633, filed Jul. 8, 2008, the contents of which are also incorporated herein by reference.

The present disclosure relates to novel cosmetic compositions with beneficial properties, intended for cleansing and protecting the color of keratin fibers such as the hair, and comprising, in a cosmetically acceptable aqueous support, at least one sulfate or sulfonate anionic surfactant, at least one surfactant chosen from amphoteric and zwitterionic surfactants, and at least one particular amino silicone, with a particular (amphoteric and/or zwitterionic surfactant)/(sulfate or sulfonate anionic surfactant) weight ratio. The disclosure also relates to the processes using of the compositions for protecting the artificial color of dyed hair.

It is a known practice to dye keratin fibers, for example human keratin fibers such as the hair, with dye compositions comprising oxidation dye precursors, which are generally known as oxidation bases. These oxidation bases are colorless or weakly colored compounds, which, when combined with oxidizing products, give rise to colored compounds via a process of oxidative condensation. It is also known that the shades obtained with these oxidation bases can be varied by combining them with couplers or coloration modifiers. The variety of molecules used as oxidation bases and couplers allows a wide range of colors to be obtained.

It is also a known practice to dye keratin fibers by direct dyeing. The process conventionally used in direct dyeing comprises applying to keratin fibers direct dyes, which are colored and coloring molecules that have affinity for the fibers, in leaving them to stand and then in rinsing the fibers.

The colorations resulting therefrom can be chromatic colorations but may be, however, only temporary or semi-permanent; this can result from the nature of the interactions that bind the direct dyes to the keratin fiber and their desorption from the surface and/or the core of the fiber being responsible for weak dyeing power and poor fastness with respect to washing.

The artificial color of the hair afforded by a direct dyeing or oxidation dyeing treatment can gradually attenuate on repeated washing and can lead over time to fading of the coloration of the hair. The use of commercial rinse-out and leave-in care products may not sufficiently improve the fastness of the artificial color of the hair.

It could thus be useful to develop methods for protecting the artificial color from the effect of repeated washing, to do so under mild conditions that are compatible with dyed hair, for example, in terms of temperature, and to improve the fastness of direct or oxidation dyeing, for example, with respect to shampoo washing.

Amino silicones have already been used for this purpose, as described in document EP 1 312 346.

The Applicant has found that the use of a detergent composition comprising a combination of surfactant and of at least one amino silicone may facilitate protection of the artificial color of keratin fibers with respect to repeated washing and thus improvement of the color fastness.

These findings form the basis of the present disclosure.

It has been found that by using the compositions according to the disclosure, the fading of the coloration after several shampoo washes can be limited. Thus, the loss of coloration, evaluated, for example, by the variation of the value of the coefficient DL* of locks before and after shampooing in the CIE L*a*b* system or alternatively by the DE* (corresponding to the square root of the sum of the squares of the variations of the coefficients L*, a* and b* of the locks before and after shampoo washing), can be reduced.

The compositions in accordance with the disclosure may also give keratin materials, for example, the hair, a noteworthy treating effect that may be manifested, for example, by providing at least one of ease of disentangling, volume, lightness, smoothness, softness or suppleness without any lank effect. The hair can look natural, clean and non-greasy.

Thus, one subject of the present disclosure is novel detergent cosmetic compositions, characterized in that they comprise, in a cosmetically acceptable aqueous medium:

(A) at least one sulfate or sulfonate anionic surfactant, (B) at least one surfactant chosen from amphoteric and zwitterionic surfactants, the (sulfate or sulfonate anionic surfactant)/(amphoteric and/or zwitterionic surfactant) weight ratio ranging from 1:1 to 2:1, and (C) at least one amino silicone having a weight-average molecular mass Mw greater than or equal to 75,000, and not comprising any quaternary ammonium groups.

A subject of the disclosure is also the cosmetic use of the above compositions for cleansing keratin fibers, for example, the hair.

Another subject of the disclosure thus relates to the use, as a pretreatment or as a post-treatment for oxidation dyeing or direct dyeing of human keratin fibers, including the hair, of a detergent composition as defined above for protecting the color with respect to washing of the artificially dyed keratin fibers.

A subject of the disclosure is also a process for protecting the color with respect to washing of artificially dyed keratin fibers, characterized in that it comprises applying to the fibers at least one detergent composition as defined above.

Another subject of the disclosure is also a process for protecting the color with respect to washing of artificially dyed keratin fibers, characterized in that it comprises applying to the fibers, before, during, or after dyeing, at least one detergent composition as defined above.

The term "human keratin fibers" means head hair or bodily hairs, for example of the beard or moustache, the eyelashes and the eyebrows, or head hair.

The expression "artificially dyed keratin fibers" means keratin fibers that have been dyed via a direct dyeing process or via an oxidation dyeing process.

The term "washing" means at least one application to the keratin fibers of an aqueous rinse-out composition, which can be a detergent composition such as a shampoo. This term also includes swimming, for example in the sea or in a swimming pool.

The various subjects of the disclosure will now be detailed. All the meanings and definitions of the compounds used in the present disclosure given above and below are valid for all of the subjects of the disclosure.

(A) Sulfate or Sulfonate Surfactants:

According to the disclosure, the sulfate or sulfonate anionic surfactants are anionic surfactants comprising at least one sulfate ($-OSO_3H$ or $-OSO_3^-$) function and/or one sulfonate ($-SO_3H$ or $-SO_3^-$) function.

The sulfate or sulfonate anionic surfactants that may be used, alone or as mixtures, in the context of the present disclosure are salts (for example alkali metal salts, such as sodium, ammonium salts, amine salts, amino alcohol salts or magnesium salts) of alkyl sulfates, alkylamido sulfates, alkyl ether sulfates, alkylamido ether sulfates, alkylaryl ether sulfates, alkyl ether sulfosuccinates, acyl isethionates, or methyl acyl taurates; in some embodiments, the alkyl or acyl radical of all these various compounds can contain from 8 to 24 carbon atoms, and/or the aryl radical can denote a phenyl or benzyl group.

The average number of ethylene oxide or propylene oxide groups may range in some embodiments from 2 to 50, for example, from 2 to 10.

Among these anionic surfactants, in some embodiments, $C_8$-$C_{14}$, or $C_{12}$-$C_{14}$ alkyl ether sulfate salts are used. These salts may in some embodiments comprise from 2 to 5 ethylene oxide groups.

In some embodiments, an anionic surfactant chosen from sodium, triethanolamine, magnesium or ammonium ($C_{12}$-$C_{14}$)alkyl sulfates, sodium, ammonium or magnesium ($C_{12}$-$C_{14}$)alkyl ether sulfates oxyethylenated with 2.2 mol of ethylene oxide, sodium cocoyl isethionate and methyltaurates may be used.

The at least one sulfate or sulfonate anionic surfactant may be present in some embodiments in an amount ranging from 2% to 20% by weight, for example from 4% to 15% by weight, from 5% to 12% by weight, or from 8% to 12% by weight relative to the total weight of the composition.

(B) Amphoteric and/or Zwitterionic Surfactant(s):

In some embodiments, the amphoteric and/or zwitterionic surfactants may, for example, be, without limitation, aliphatic secondary or tertiary amine derivatives in which the aliphatic radical is a linear or branched chain containing 8 to 22 carbon atoms and containing at least one water-soluble anionic group (for example carboxylate, sulfonate, sulfate, phosphate or phosphonate); mention may also be made of ($C_8$-$C_{20}$)alkylbetaines, sulfobetaines, ($C_8$-$C_{20}$)alkylamido($C_1$-$C_6$)alkylbetaines or ($C_8$-$C_{20}$)alkylamido($C_1$-$C_6$)alkyl-sulfobetaines.

Among the amine derivatives, mention may be made of the products as described in U.S. Pat. No. 2,528,378 and U.S. Pat. No. 2,781,354 and having the structures:

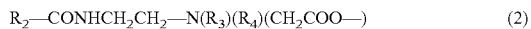

$$R_2\text{—CONHCH}_2\text{CH}_2\text{—N}(R_3)(R_4)(\text{CH}_2\text{COO—})  \quad (2)$$

in which: $R_2$CO denotes a $C_6$-$C_{24}$ acyl radical, for example a radical present in hydrolysed coconut oil, an octyl, decoyl or dodecanoyl radical, and mixtures thereof, $R_3$ denotes a β-hydroxyethyl group and $R_4$ a carboxymethyl group; and

$$R_{2'}\text{—CONHCH}_2\text{CH}_2\text{—N}(B)(C) \quad (3)$$

in which:
B represents —$CH_2CH_2OX'$, C represents —$(CH_2)_z$—Y', with z=1 or 2, X' denotes the —$CH_2CH_2$—COOH group or a hydrogen atom, Y' denotes —COOH or the —$CH_2$—CHOH—$SO_3H$ radical, R'$_2$CO denotes a C6-C24 acyl radical, for example a radical present in hydrolysed coconut oil or linseed oil, or an octyl, decoyl or dodecanoyl, stearoyl, isostearoyl or oleoyl radical, and mixtures thereof.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caproloamphodipropionate, lauroamphodipropionic acid, cocoamphodipropionic acid.

An example that may be mentioned is disodium cocoamphodiacetate, sold under the trade name Miranol® C2M Concentrate by the company Rhodia Chimie.

In some embodiments at least one amphoteric and/or zwitterionic surfactant belonging to the betaine group such as alkylbetaines, such as the cocoylbetaine sold under the name Dehyton AB 30 as an aqueous solution containing 30% AM by the company Henkel, or at least one alkylamidobetaine, for instance cocamidopropylbetaine, such as TEGOBETAINE® F50 sold by the company Goldschmidt is used.

In some embodiments, the at least one amphoteric and/or zwitterionic surfactant can be present in an amount ranging from 2% to 20% by weight, for example, from 5% to 10% by weight relative to the total weight of the composition.

In the composition, the (sulfate or sulfonate anionic surfactant)/(amphoteric and/or zwitterionic) surfactant weight ratio ranges from 1:1 to 2:1. In some embodiments, it ranges from 1.2:1 to 1.9:1, or from 1.5:1 to 1.9:1.

In some embodiments, the composition may comprise at least one other surfactant, for example, at least one carboxylic anionic surfactant.

The at least one carboxylic anionic surfactant may in some embodiments be present in concentrations ranging from 0.5% to 10% by weight, for example, from 1% to 5% by weight relative to the total weight of the composition.

In some embodiments, the total weight of surfactants may represent from 4% to 35% by weight, for example from 6% to 25% by weight or from 8% to 20% by weight, relative to the total weight of the final composition.

(C) Amino Silicone:

The term "amino silicone" denotes any silicone comprising at least one primary, secondary or tertiary amine. Amino silicones do not comprise any quaternary ammonium groups.

In some embodiments, the composition comprises at least one amino silicone chosen from amino silicones of formula (I) below:

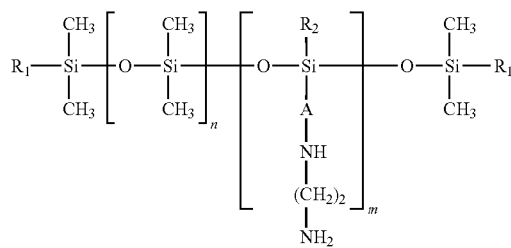

in which:
A denotes a linear or branched $C_2$-$C_8$ alkylene radical, m and n are numbers such that the weight-average molecular mass Mw is greater than or equal to 75,000 Da, and $R_1$ and $R_2$ denote, independently of each other, a $C_1$-$C_4$ alkyl radical or a $C_1$-$C_4$ alkoxy radical or a hydroxyl radical.

In some embodiments, the radicals $R_1$ are identical and denote a hydroxyl radical.

In some embodiments, the viscosity of the at least one amino silicone is greater than 25,000 mm$^2$/s measured at 25° C., or ranges from 30,000 to 200,000 mm$^2$/s at 25° C., from 50,000 to 150,000 mm$^2$/s, or from 70,000 to 120,000 mm$^2$/s, measured at 25° C. The viscosities of the silicones are measured, for example, according to the standard ASTM 445 Appendix C.

In some embodiments, the cationic charge of the at least one amino silicone is less than or equal to 0.5 meq./g, for example ranging from 0.01 to 0.1 meq./g or from 0.03 to 0.06 meq./g.

In some embodiments, the at least one amino silicone has a weight-average molecular mass ranging from 75,000 to 1 000,000 Da, or from 100,000 to 200,000 Da.

The weight-average molecular masses of the at least one amino silicone can be measured by gel permeation chromatography (GPC) at room temperature, as polystyrene equivalents. The columns used are µ styragel columns. The eluent is THF and the flow rate is 1 ml/minute. 200 µl of a solution containing 0.5% by weight of silicone in THF are injected. Detection is performed by refractometry and UV-metry.

In some embodiments, the at least one amino silicone can be in the form of an oil-in-water emulsion.

The oil-in-water emulsion may comprise at least one surfactants. The surfactants may be of any nature. In some embodiments, the surfactants can be, for example, cationic and/or nonionic.

The silicone particles in the emulsion have a volume-average diameter D[4.3] that can range from 10 nm to 1000 nm, for example, from 50 nm to 800 nm, from 100 nm to 600 nm, or from 200 nm to 500 nm. These particle sizes may be determined using a laser granulometer, for example the Malvern Mastersizer 2000 granulometer.

An amino silicone corresponding to this formula is, for example, DOW CORNING 2-8299® Cationic Emulsion from the company Dow Corning.

In some embodiments, the at least one amino silicone is used in an amount ranging from 0.01% to 20% by weight relative to the total weight of the composition, for example, from 0.05% to 10% by weight, from 0.1% to 5% by weight, or from 0.5% to 3% by weight relative to the total weight of the composition.

In some embodiments, the compositions may also comprise at least one water-soluble salt and/or at least one water-soluble monohydroxylated or polyhydroxylated alcohol. The at least one water-soluble salt can be for example chosen from the salts of monovalent and divalent metals and of a mineral and organic acid.

Mention may be made, for instance, of sodium chloride, potassium chloride, calcium chloride, magnesium sulfate, sodium citrate and the sodium salts of phosphoric acid.

Water-soluble monohydroxylated or polyhydroxylated alcohols that may be mentioned include, for example, ethanol, isopropanol, propylene glycol, glycerol and hexylene glycol.

In some embodiments, the detergent compositions have a final pH ranging from 2 to 8, for example, from 3 to 7.5. The pH may be adjusted to the desired value conventionally by adding a base (organic or mineral) to the composition, for example, sodium hydroxide, aqueous ammonia or a primary, secondary or tertiary (poly)amine, for instance, monoethanolamine, diethanolamine, triethanolamine, isopropanolamine or 1,3-propanediamine, or alternatively by adding a mineral or organic acid, for example citric acid or hydrochloric acid.

The cosmetically acceptable aqueous medium may be constituted solely of water or of a mixture of water and of at least one cosmetically acceptable solvent, for example, the monohydroxylated or polyhydroxylated alcohols mentioned above or ethers of these alcohols, esters or ketones.

In some embodiments, the composition for example comprises at least 30% by weight, for example from 50% to 90% by weight or from 70% to 85% by weight of water relative to the total weight of the composition.

In some embodiments, the composition comprises less than 20% by weight of fatty phase relative to the total weight of the composition.

The fatty phase comprises all the fatty substances of the composition that are insoluble in water at room temperature, such as, for example, fatty esters, plant, mineral or synthetic oils, fatty alcohols, fatty acids, fatty amides, waxes and silicones. The fatty phase may in some embodiments range from 0.1% to 15% by weight, for example, from 0.5% to 10% by weight or from 0.5% to 8% by weight, relative to the total weight of the composition.

In some embodiments, the composition may contain, in addition to the combination defined above, at least one viscosity regulator, such as a thickener. Mention may be made of scleroglucans, xanthan gums, fatty acid alkanolamides, alkyl ether carboxylic acid alkanolamides optionally oxyethylenated with up to 5 mol of ethylene oxide, such as the product sold under the name Aminol A15 by the company Chem Y, crosslinked polyacrylic acids and crosslinked acrylic acid/ $C_{10}$-$C_{30}$ alkyl acrylate copolymers. These viscosity regulators can be used in the compositions in proportions that may be up to 10% by weight relative to the total weight of the composition. Crosslinked polyacrylic acids, for instance CARBOPOL 980 from Noveon, can also be used.

The compositions may also contain up to 5% of at least one nacreous agent and/or opacifier that are well known in the state of the art, for instance fatty alcohols, sodium palmitate or magnesium palmitate, sodium or magnesium stearate or hydroxystearate, fatty alcohols, fatty-chain acyl derivatives such as ethylene glycol or polyethylene glycol distearates, fatty-chain ethers, for instance distearyl ether or 1-(hexadecyloxy)-2-octadecanol, and cyclodextrins, for instance, β-cyclodextrins.

The compositions may also optionally contain at least one other agent which can have the effect of improving the cosmetic properties of the hair or the skin without, however, impairing the stability of the compositions. Mention may be made in this respect of cationic surfactants, anionic, nonionic, cationic or amphoteric polymers, proteins, protein hydrolysates, ceramides, pseudoceramides, plant oils, fatty acids, for example containing linear or branched $C_{16}$-$C_{40}$ chains such as 18-methyleicosanoic acid, hydroxy acids, vitamins, provitamins such as panthenol, volatile or non-volatile silicones other than the amino silicones of formula (I) or (II), which are soluble or insoluble in the medium, UV-screening agents, moisturizers, antidandruff or anti-seborrhoeic agents, hair-loss counteractants and free-radical scavengers, and mixtures thereof.

In some embodiments, the composition also comprises at least one non-silicone cationic polymer.

The cationic polymers that may be used may be chosen from any of those already known per se as improving the cosmetic properties of hair treated with detergent compositions, for example those described in patent application EP-A-0 337 354 and French patent applications FR-A-2 270 846, 2 383 660, 2 598 611, 2 470 596 and 2 519 863.

Even more generally, for the purposes of the present disclosure, the term "cationic polymer" denotes any polymer containing cationic groups and/or groups that can be ionized into cationic groups.

The cationic polymers that may be used may in some embodiments have a cationic charge density of greater than or equal to 0.01 meq./g, for example, ranging from 0.1 to 10 meq./g or from 3 to 8 meq./g.

In some embodiments, at least one cationic polymer may be used that is chosen from quaternary cellulose ether derivative, for example, the products sold under the name JR 400 by the company Union Carbide Corporation, cyclopolymers, e.g., diallyldimethylammonium salt homopolymers such as Merquat 100, and copolymers of a diallyldimethylammonium salt and of acrylamide, e.g., the chlorides sold under the names MERQUAT 550 and MERQUAT S by the company Merck, guar gums modified with 2,3-epoxypropyltrimethylammonium chloride, sold, for example, under the name Jaguar C13S by the company Rhodia Chimie, optionally crosslinked homopolymers and copolymers of (meth)acryloyloxyethyltrimethylammonium salt, sold by the company Ciba as a 50% solution in mineral oil under the trade names SALCARE SC92 (crosslinked copolymer of methacryloyloxyethyltrimethylammonium chloride and of acrylamide) and SALCARE SC95 (crosslinked homopolymer of methacryloyloxyethyltrimethylammonium chloride), quaternary copolymers of vinylpyrrolidone and of a vinylimidazole salt such as the products sold by BASF under the names LUVIQUAT FC 370, LUVIQUAT FC 550, LUVIQUAT FC 905 and LUVIQUAT HM-552.

In some embodiments, the at least one cationic polymer can be present in an amount ranging from 0.005% to 10% by weight, for example from 0.01% to 5% by weight, or from 0.1% to 3% by weight relative to the total weight of the final composition.

In some embodiments, the composition may also contain at least one foam synergist such as $C_{10}$-$C_{18}$ 1,2-alkanediols or $C_{10}$-$C_{18}$ fatty alkanolamides derived from monoethanolamine or from diethanolamine.

Needless to say, a person skilled in the art will take care to select this or these optional additional compound(s) and/or the amounts thereof such that the stability of the composition and the cosmetic properties intrinsically associated with the composition in accordance with the disclosure are not, or are not substantially, adversely affected by the envisaged addition(s).

In some embodiments, the composition may be transparent.

The transparency may be measured by measuring the transmittance at 700 nm via a spectrometer (for example a Lambda 14 spectrometer from Perkin-Elmer or a UV2101 PC spectrometer from Shimadzu). The transparent compositions have a transmittance of greater than or equal to 94%, and for example ranging from 96% to 100%.

These compositions may be in the form of more or less thickened liquids, creams or gels, and they can be suitable for washing and caring for keratin fibers, for example, the hair.

A subject of the disclosure is also a process for washing and conditioning keratin fibers, for example, the hair, which comprises applying to the wet keratin materials an effective amount of a composition as defined above, and then in rinsing with water after an optional leave-in time.

The compositions according to the disclosure can be used as shampoos for washing and conditioning the hair, and they are applied, in this case, to wet hair in amounts that are suitable to wash them, and the lather generated by massaging or rubbing with the hands is then removed after an optional leave-in time, by rinsing with water, the operation possibly being repeated one or more times.

Concrete but in no way limiting examples illustrating the disclosure are given below.

EXAMPLE 1

The following shampoo composition in accordance with the disclosure was prepared.

| | 1 |
|---|---|
| Sodium lauryl ether sulfate (70/30 C12/C14) containing 2.2 mol of ethylene oxide, as an aqueous solution containing 70% AM | 11.55 g AM |
| Cocamidopropylbetaine at 38% AM (TEGOBETAINE F 50 from Goldschmidt) | 5.5 g AM |
| Sodium N-cocoylamidoethyl-N-ethoxycarboxymethyl-glycinate as an aqueous solution containing 31.5% active material (MIRANOL C2M Conc. from Rhodia Chimie) | 0.95 g AM |
| Amino silicone as an aqueous emulsion containing 57.5% AM (DC2-8299 from Dow Corning) | 1.55 g AM |
| Copolymers of polydimethyldiallylammonium chloride and of acrylamide in water at 8% active material (MERQUAT 550 from Nalco) | 0.24 g AM |
| Crosslinked polyacrylic acid (CARBOPOL 980 from Noveon) | 0.2 g |
| Ethylene glycol distearate | 2.5 g |
| Salicylic acid | 0.2 g |
| Fragrance, preserving agent | qs |
| pH agent, qs pH | qs pH 5.3 |
| Demineralized water, qs | 100 g |

Hair treated with this composition disentangled easily and was light and smooth from the root to the end.

Artificially dyed hair treated with this composition had better color fastness with respect to repeated shampooing.

EXAMPLE 2

The following shampoo compositions were prepared:

| | 2 (disclosure) | A |
|---|---|---|
| Sodium lauryl ether sulfate (70/30 C12/C14) containing 2.2 mol of ethylene oxide, as an aqueous solution containing 70% AM | 11.55 g AM | 7 g AM |
| Cocobetaine at 30% AM (DEHYTON AB 30 from Cognis) | 6.45 g AM | 2.5 g AM |
| Amino silicone as an aqueous emulsion containing 57.5% AM (DC2-8299 from Dow Corning) | 1.8 g AM | 1.8 g AM |
| Hydroxyethylcellulose quaternized with 2,3-epoxypropyl trimethylammonium (UCARE Polymer JR 400 from Amerchol) | 0.4 g AM | 0.4 g AM |
| Ethylene glycol distearate | 1.5 g | 1.5 g |
| Acrylic polymer emulsion (AQUA SF1 from Noveon) | 0.8 g AM | 0.8 g AM |
| Preserving agent | qs | qs |
| Citric acid or NaOH, qs pH | 5.5 | 5.5 |
| Demineralized water, qs | 100 g | 100 g |
| (Sulfate or sulfonate anionic surfactant)/(amphoteric and/or zwitterionic surfactant) weight ratio | 1.79:1 | 2.8:1 |

After eight shampoo washes (0.4 g of shampoo per g of hair), a DE (color difference before and after treatment by the 8 shampoo washes) of 11.95 was obtained on permanent-waved natural hair containing 90% grey hairs dyed with a Majirouge 6.66 dye from L'Oreal (4 g of cream and 6 g of 20-volumes oxidizing agent), as opposed to a DE of 14.05 obtained for hair treated with shampoo A. The smaller the value of DE, the more efficient the protection.

Thus, artificially dyed hair treated with composition 2 containing a ratio according to the present disclosure showed better color fastness with respect to repeated shampooing than that treated with composition A.

What is claimed is:

1. A detergent cosmetic composition, characterized in that it comprises, in a cosmetically acceptable aqueous medium:
   (A) at least one sulfate or sulfonate anionic surfactant, (B) at least one surfactant chosen from amphoteric and zwitterionic surfactants, the (sulfate or sulfonate anionic surfactant)/(amphoteric and/or zwitterionic surfactant) weight ratio ranging from 1.2:1 to 2:1 and the total amount of surfactants representing from 6% to 25% by weight relative to the total weight of the final composition, and (C) at least one amino silicone having a weight-average molecular mass Mw ranging from 100,000 to 200,000 Da, and not comprising any quaternary ammonium groups, and further being present in a concentration ranging from 0.05% to 10% by weight relative to the total weight of the composition.

2. The composition according to claim 1, characterized in that the at least one sulfate or sulfonate anionic surfactant is present in a concentration ranging from 2% to 20% by weight relative to the total weight of the composition.

3. The composition according to claim 1, characterized in that the at least one sulfate or sulfonate anionic surfactant is present in a concentration ranging from 4% to 15% by weight relative to the total weight of the composition.

4. The composition according to claim 1, characterized in that the at least one amphoteric and/or zwitterionic surfactant is present in a concentration ranging from 2% to 20% by weight relative to the total weight of the composition.

5. The composition according to claim 1, characterized in that the at least one amphoteric and/or zwitterionic surfactant is present in a concentration ranging from 5% to 10% by weight relative to the total weight of the composition.

6. The composition according to claim 1, characterized in that the (sulfate or sulfonate anionic surfactant)/(amphoteric and/or zwitterionic surfactant) weight ratio ranges from 1.2:1 to 1.9:1.

7. The composition according to claim 1, characterized in that the (sulfate or sulfonate anionic surfactant)/(amphoteric and/or zwitterionic surfactant) weight ratio ranges from 1.5:1 to 1.9:1.

8. The composition according to claim 1, characterized in that the at least one amino silicone is chosen from amino silicones of formula (I) below:

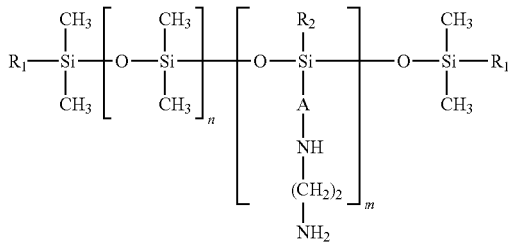

in which:
A denotes a linear or branched $C_2$-$C_8$ alkylene radical,
m and n are numbers such that the weight-average molecular mass Mw ranging from 100,000 to 200,000 Da, and
$R_1$ and $R_2$ denote, independently of each other, a $C_1$-$C_4$ alkyl radical or a $C_1$-$C_4$ alkoxy radical or a hydroxyl radical.

9. The composition according to claim 8, characterized in that A denotes a linear or branched $C_3$ alkylene radical.

10. The composition according to claim 8, characterized in that at least one R1 of the at least one amino silicone is a hydroxyl radical.

11. The composition according to claim 8, characterized in that at least one R1 of the at least one amino silicone is a $C_1$-$C_4$ alkoxy radical.

12. The composition according to claim 1, characterized in that the viscosity of the at least one amino silicone ranges from 30,000 to 200,000 mm$^2$/s at 25° C.

13. The composition according to claim 1, characterized in that the cationic charge of the amino silicone is less than or equal to 0.1 meq./g.

14. The composition according to claim 1, characterized in that the at least one amino silicone is present in a concentration ranging from 0.5% to 3% by weight relative to the total weight of the composition.

15. The composition according to claim 1, characterized in that the at least one amino silicone is present in a concentration ranging from 0.1% to 5% by weight relative to the total weight of the composition.

16. The composition according to claim 1, characterized in that it also comprises at least one carboxylic anionic surfactant.

17. The composition according to claim 1, characterized in that the composition also comprises at least one non-silicone cationic polymer.

18. The composition according to claim 17, characterized in that the at least one non-silicone cationic polymer is chosen from diallyldimethylammonium salt homopolymers.

19. The composition according to claim 17, characterized in that the at least one non-silicone cationic polymer is present in a concentration ranging from 0.005% to 10% by weight relative to the total weight of the final composition.

20. The composition according to claim 17, characterized in that the at least one non-silicone cationic polymer represents from 0.1% to 3% by weight relative to the total weight of the final composition.

21. The composition according to claim 1, characterized in that the at least one amino silicone is present as an oil-in-water emulsion in which the volume-average diameter D[4.3] ranges from 50 nm to 800 nm.

22. A detergent cosmetic composition, characterized in that it comprises, in a cosmetically acceptable aqueous medium:
(A) at least one sulfate or sulfonate anionic surfactant,
(B) at least one surfactant chosen from amphoteric and zwitterionic surfactants, the (sulfate or sulfonate anionic surfactant)/(amphoteric and/or zwitterionic surfactant) weight ratio ranging from 1.5:1 to 1.9:1 and the total amount of surfactants representing from 6% to 25% by weight relative to the total weight of the final composition,
(C) at least one amino silicone present in a concentration ranging from 0.05% to 10% by weight relative to the total weight of the composition as an oil-in-water emulsion in which the volume-average diameter D[4.3] ranges from 50 nm to 800 nm, the at least one amino silicone being chosen from those of formula (I) below:

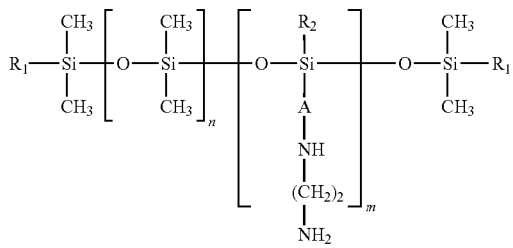

in which:
A denotes a linear or branched $C_3$ alkylene radical, m and n are numbers such that the weight-average molecular mass Mw ranges from 100,000 Da to 200,000 Da,
the cationic charge of the amino silicone is less than or equal to 0.1 meq./g, and
$R_1$ and $R_2$ denote, independently of each other, a $C_1$-$C_4$ alkoxy radical or a hydroxyl radical,
- (D) at least one carboxylic anionic surfactant, and
- (E) at least one non-silicone cationic polymer chosen from diallyldimethylammonium salt homopolymers.

23. A process for protecting the color with respect to washing of artificially dyed keratin fibers, fiber comprising applying to the fibers, before or after dyeing the fibers, at least one composition comprising, in a cosmetically acceptable aqueous medium:
- (A) at least one sulfate or sulfonate anionic surfactant,
- (B) at least one surfactant chosen from amphoteric and zwitterionic surfactants, the (sulfate or sulfonate anionic surfactant)/(amphoteric and/or zwitterionic surfactant) weight ratio ranging from 1.2:1 to 2:1 and the total amount of surfactants representing from 6% to 25% by weight relative to the total weight of the final composition, and
- (C) at least one amino silicone having a weight-average molecular mass Mw ranging from 100,000 to 200,000 Da, and not comprising any quaternary ammonium groups, and further being present in a concentration ranging from 0.05% to 10% by weight relative to the total weight of the composition.

* * * * *